US005573756A

United States Patent [19]
Lambrechts

[11] Patent Number: 5,573,756
[45] Date of Patent: Nov. 12, 1996

[54] SHAMPOO CONDITIONER AND SOFTGEL FILLED THEREWITH

[75] Inventor: John Lambrechts, Burbank, Calif.

[73] Assignee: Banner Pharmacaps Inc., Chatsworth, Calif.

[21] Appl. No.: 377,378

[22] Filed: Jan. 25, 1995

[51] Int. Cl.$^6$ .............................. A61K 7/075; A61K 9/48
[52] U.S. Cl. .................. 424/70.24; 424/70.1; 424/70.22; 424/456
[58] Field of Search ........................ 424/456, 401, 424/70.1, 70.22, 70.24

[56] References Cited

U.S. PATENT DOCUMENTS

| | | | |
|---|---|---|---|
| 3,590,122 | 6/1971 | Hutcheson et al. | 424/70 |
| 3,808,329 | 4/1974 | Bolich, Jr. et al. | 424/70 |
| 3,816,616 | 6/1974 | Anguillo et al. | 424/70 |
| 4,272,515 | 6/1981 | Hofman et al. | 424/70 |
| 4,701,322 | 10/1987 | Dixon et al. | 424/70 |
| 5,089,269 | 2/1992 | Noda et al. | 424/456 |

OTHER PUBLICATIONS

"Cocamide DEA,"International Cosmetic Ingredient Dictionary, Fifth Edition, Washington, D.C. (1993), vol. 1, p. 157.
"PEG–Glyceryl Cocoate"International Cosmetic Ingredient Dictionary, Fifth Edition, Washington, D.C. (1993), vol. 1, p. 491.
"Polyquaternium–10," International Cosmetic Ingredient Dictionary, Fifth Edition, Washington, D.C. (1993), vol. 1, p. 571.

Primary Examiner—Jyothsna Venkat
Attorney, Agent, or Firm—Jeffer, Mangels, Butler & Marmaro LLP

[57] ABSTRACT

An shampoo conditioner composition which is capable of being stably encapsulated within a gelatin shell includes a concentrated surfactant, a cationic conditioner, and a carrier, and has an equilibrium relative humidity (ERH) of less than about 65%.

19 Claims, No Drawings

SHAMPOO CONDITIONER AND SOFTGEL FILLED THEREWITH

FIELD OF THE INVENTION

The present invention relates to an improved shampoo conditioner formulation. More particularly, the invention relates to a shampoo conditioner formulation which is suitable for use as a fill in a gelatin capsule.

BACKGROUND OF THE INVENTION

Contemporary standards of personal hygiene require regular cleaning of the hair to maintain a presentable appearance. Modern shampoo compositions effectively clean the hair, by removing excess soil and sebum, and can also include additional ingredients such as conditioners. Exemplary conditioners and conditioning shampoo formulations are disclosed by Roberts et al., U.S. Pat. No. 3,590,122; Bolich et al., U.S. Pat. No. 3,808,329; Angvillo et al., U.S. Pat. No. 3,816,616; Hofman et al., U.S. Pat. No. 4,272,515; and Dixon et al., U.S. Pat. No. 4,701,322.

Shampoo and shampoo/conditioner compositions have hitherto been formulated for packaging and dispensing from conventional containers, such as plastic bottles, tubes, etc. With the development of the soft gelatin capsule, or softgel, an alternative form of dispensing and applying shampoos has become available. Encapsulation of a shampoo composition in a softgel offers numerous advantages. For example, no additional packaging would be needed for the shampoo-filled softgels. The shampoo could be prepared in pre-measured quantities sufficient for cleaning the hair, thus minimizing shampoo waste. The shampoo could be dispensed from the softgel while the user is showering, typically by squeezing or breaking the softgel, and the empty softgel could then be disposed of simply and easily, for example by dropping it to the floor of the shower to dissolve.

For practicable encapsulation within a softgel, however, a shampoo composition must be compatible with the softgel. In particular, the shampoo composition must be formulated such that it can be stably encapsulated in the softgel shell without dissolving the softgel. The shampoo composition should be formulated such that it is stable in encapsulated form for extended periods of time at room temperature.

A need exists for a shampoo/conditioner composition that is compatible with a softgel shell and can be encapsulated stably in a softgel.

SUMMARY OF THE PREFERRED EMBODIMENTS

In accordance with one aspect of the present invention, there is provided a shampoo conditioner composition which is capable of being stably encapsulated within a gelatin shell. Preferably, the inventive composition has an equilibrium relative humidity of less than about 65%.

In a preferred embodiment, the inventive composition includes a cationic conditioner, and a carrier. Very preferably, the composition also includes a humectant.

According to another aspect of the present invention, a hair care product includes a shampoo conditioner composition as described above, encapsulated in a gelatin shell.

According to a further aspect of the present invention, a method of shampooing hair includes the steps of dispensing a shampoo conditioner composition encapsulated in a hair care product as described above from its gelatin shell, applying the composition to the hair, which has been wet with water, working the composition through the hair, and rinsing the composition from the hair.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

As used herein, a "shampoo conditioner" denotes a shampoo that includes a conditioning agent that is effective in improving the appearance or manageability of hair, e.g., making the hair easier to comb when wet.

Applicant has discovered that shampoo conditioner compositions that are useful in combination with soft gelatin shells can be prepared by limiting the amount of active, or "free", water in the composition. The low amount of free water in the inventive compositions ensures that the compositions do not adversely interact with soft gelatin shells, e.g., by migration of free water, surfactant, etc., into the gelatin shells. In general, a composition according to the invention includes an excessive amount of free water if soft spots form in a gelatin shell within which the composition is encapsulated.

More particularly, shampoo conditioner compositions according to the invention preferably have a very low equilibrium relative humidity (ERH). The ERH is a measure of the amount of water in a composition that is free, or "active." In most compositions containing water, at least a portion of the water molecules is strongly bound to various sites, in particular polar sites, on the various chemical constituents of the composition. Such sites include hydroxyl groups, carbonyl groups, amino groups, and other sites that are capable of binding water by hydrogen bonding, ionic bonding, etc. Additional quantities of water molecules may be bound less strongly, yet still be effectively unavailable as a solvent for the composition or for materials with which the composition comes into contact. The remaining water is unbound, that is, free.

The ERH of a composition is measured by determining the humidity, in an enclosed volume, at which the vapor pressure of water contained in the composition is equal to the vapor pressure of water in the volume of air above the composition. ERH, and the related quantity of water activity (obtained by dividing the measured ERH by 100), can readily be measured using instruments available commercially from, e.g., Rotronic Instrument Corp. (Huntington, N.Y.). Various methods for measuring ERH and water activity are described in R. Marsili, "Water Activity: Why It's Important and How to Measure It," *Food Product Design*, December 1993, pp. 36–41, which is incorporated herein by reference.

Compositions having an ERH of less than about 65%, more preferably between about 65% and 35%, have proven suitable for encapsulation according to the invention and are therefore preferred.

The inventive compositions preferably include a surfactant, a cationic conditioner, and a carrier. The surfactant preferably is a concentrated surfactant, i.e., a surfactant which includes a reduced amount of water, and thus a reduced amount of free water. Concentrated surfactants are preferred in order to meet the requirement that the composition is capable of being stably encapsulated in a softgel. Preferably, the surfactant is concentrated to at least about 60% by weight.

Useful surfactants according to the invention include anionic surfactants having detergent action, preferably sulfonated and sulfated anionic detergents. Such surfactants include sodium, magnesium, ammonium and mono-, di- and triethanolamine salts of sulfated fatty alcohols and sulfonated alkaryl compounds, preferably those having a total of from 12 to 21 carbon atoms. Exemplary surfactants include sodium laureth sulfate, sodium lauryl sulfate, ammonium lauryl sulfate, sodium oleyl succinate, triethanolamine oleate, and the like. Useful anionic detergents are disclosed in U.S. Pat. No. 3,932,610, to Rudy et al., which is incorporated in its entirety herein by reference. Combinations of two or more surfactants can also be used.

Sodium laureth sulfate is particularly preferred because it provides a lather having fine bubbles. Other surfactants may afford larger bubbles, which are less desirable.

The surfactant or surfactant combination preferably comprises at least about 10% by weight of the inventive composition in order to afford a shampoo with desirable hair cleaning properties. The upper limit on the amount of surfactant is determined by the quantity of free water present in the composition. More preferably, the upper limit on the amount of surfactant is that amount at which the shampoo composition has an ERH of about 65%. In general, surfactants that are highly concentrated (about 60% or more) can be used in the inventive compositions in amounts up to about 40% by weight.

The cationic conditioner preferably is a quaternary ammonium salt such as polyquaternium-10 (a resin powder commercially available as Polymer JR-400, from Amerchol) or Alacsan 7LUF (a modified alkyl dimethylbenzyl ammonium chloride commercially available from Alcolac Chemical Corp.), an amine salt such as Richamate 3225 (commercially available from The Richardson Co.), Miramine SH (a mixture of tertiary and quaternary amine derivatives commercially available from Miranol Chemical Co., Inc.), Sole-Onic QS-80 (a quaternary imidazoline commercially available from Sole Chemical Corp.) and the like. Combinations of cationic conditioners can also be used.

Polyquaternium-10 is particularly preferred because it functions as a thickening agent, as well as a conditioning agent, when used in combination with a carrier such as a polyethylene glycol (PEG). Other conventional cationic conditioners can also be employed, but it may be necessary or useful to employ a thixotropic agent, such as a Myglyol gel (commercially available from Huls America, Inc.), with such conditioners to adequately thicken the composition.

The cationic conditioner or combination of conditioners preferably is present in an amount from about 1–5 wt %. Conditioners which are less concentrated (e.g., Miramine SH [34%]) should be used in lower amounts within the foregoing range in order to minimize the amount of free water in the compositions.

The shampoo compositions of the invention also include a carrier or combination of carriers. The carrier or combination of carriers preferably is hydrophilic, and is compatible with the other ingredients of the composition. In particular, useful carriers are compatible with gelatin in order to afford a composition that can be encapsulated stably in a softgel. Preferred carriers include polyalkylene glycols, particularly those having a weight average molecular weight from about 200 to about 800. Exemplary polyalkylene glycols useful according to the invention include polyethylene glycol 400 (PEG-8), commercially available from Ashland Chemical. The carrier or combination of carriers comprise the balance of the shampoo compositions, typically about 35–60 wt % of the compositions.

In a more specific preferred embodiment, the shampoo conditioner includes a humectant or combination of humectants. Exemplary humectants include PEG-7 glyceryl cocoate (commercially available as Cetiol HE from Henkel), cocamide DEA (commercially available as Monsterge 779 from Mons), ethoxylated methyl glucosides, such as Glucuat 125 (commercially available from Amerchol), and similar materials. Humectants or combinations of humectants can be present in the shampoo composition in amounts up to about 15 wt %.

Optionally, the shampoo conditioner compositions can include at least one additional ingredient, preferably a conventional additive such as a non-cationic (preferably non-ionic) hair conditioner, a pH adjuster, a foam enhancer, a clarifier and/or a fragrance. Preferred non-cationic hair conditioners include tocopherol (Vitamin E) and bisabolol, very preferably a combination of the two conditioners, as well as other conventional non-cationic conditioning agents that are compatible with the other ingredients of the shampoo compositions (i.e., do not separate from the compositions or adversely interact with the other ingredients) and with gelatin.

Non-cationic conditioning agents, if employed, can be present in total amounts up to about 2 wt % of the shampoo composition, typically about 0.1 to 2 wt %, preferably about 0.5 wt % of the composition. Very preferably, when Vitamin E and/or bisabolol are included in the inventive compositions, one or more humectants, in particular those specified above, are also included. The humectants function to prolong contact between these conditioning agents and the hair.

If desired, a pH adjusting ingredient can be added to the inventive shampoo composition. Such ingredients can be used to reduce the pH of the inventive compositions from basic, typically around pH 10, to less basic or more neutral. Suitable pH adjusters include acids such as citric acid, lactic acid, glycolic acid and other similar weak acids known for such use. Preferably, the selected acid is concentrated to at least about 50% in order to minimize the amount of free water in the composition.

However, pH adjusters should be used with care. Some pH adjusters, in particular citric acid, can cause cloudiness in the shampoo compositions. Citric acid reacts with excess (free) sodium ions, in particular sodium ions from the surfactants, such as sodium laureth sulfate. The sodium ions act to stabilize the surfactants, and their removal by citric acid tends to destabilize the surfactant and promote the formation of micelles. Micelles cause the shampoo compositions to appear cloudy rather than clear. In addition, micelles generally have a higher water content than the bulk shampoo composition, and tend to migrate toward the bottom of the softgel and into the gelatin shell thereof when the compositions are encapsulated within a softgel. This migration results in penetration of water and surfactant into the shell, causing soft spots. Thus, the quantity of citric or other acid pH adjuster employed preferably is controlled to minimize cloudiness, micelle formation and the occurrence of soft spots.

If used, pH adjusters are preferably present in amounts up to about 0.5 wt % (exclusive of carriers or diluents).

Optional foam enhancers can be employed to increase sudsing power and foam stability. Exemplary foam enhancers include cocoamide, lauric diethanolamide and lauric isopropanol amide. Other exemplary foam enhancers are described in Rudy et al., U.S. Pat. No. 3,932,610. Foam enhancers, if employed, should be compatible with the other ingredients of the fill and with gelatin.

Clarifying agents can also be employed if desired, in order to reduce the formation of micelles. Exemplary clarifying agents include alcohols such as ethanol. If alcohols are employed, they preferably are present in an amount not exceeding about 1 wt %, more preferably not exceeding about 0.5 wt %. Larger amounts of alcohols can cause excessive softening of gelatin shells, making the compositions unsuitable for encapsulation in softgels.

Fragrances such as perfume oils and the like can be added if desired. Typically the amount of fragrance can range up to about 2 wt %.

Preferably, the shampoo compositions of the present invention have a viscosity in the range from about 5000 to 8000 cps (measured at 25° C.), more preferably about 7000 cps.

The inventive shampoo conditioner compositions can be packaged in conventional packaging such as plastic bottles, tubes, etc. A user can thus dispense the inventive shampoos from a conventional bottle or tube, apply the composition to his or her hair, which has been wet with water, work the composition through the hair, and rinse the composition from the hair.

The inventive compositions are particularly suitable for encapsulation in a soft gelatin shell, or softgel (a one-piece, hermetically sealed soft gelatin shell containing a liquid, a suspension, or a semi-solid). Thus, according to a preferred embodiment, a user can dispense the shampoo composition from such an encapsulating gelatin shell, and apply the shampoo composition as described above to his or her hair.

Softgels including the inventive shampoo compositions can be produced using any conventional manufacturing process. The most common modern manufacturing process involved in the preparation of softgels is a continuous method whereby two gelatin ribbons pass between twin rotating dies. As the ribbons meet, the liquid to be encapsulated is precisely injected between them. The capsule halves are sealed and ejected by the continuous rotation of the dies. See P. Tyle, *Specialized Drug Delivery Systems*, Marcel Dekker, Inc. (1990) for a general discussion of softgel manufacturing and production technology, in particular, Chapter 10 by Paul K. Wilkinson and Foo Song Hom.

Various gelatin shell masses may be prepared, depending on the fill properties, climatic conditions, and end use. Typically gelatin formulations include the same basic ingredients, namely, gelatin, a plasticizer such as glycerin, water, and optionally preservatives. The formulations of gelatins are well known to those of ordinary skill in the art.

The typical rotary die process, which requires a flowable liquid or fill, is readily adaptable to accommodate the shampoo compositions of the instant invention.

Shell formulations are discussed in Van Hostetler and J. Q. Bellard noted below as well as in "Advances in Softgel Formulation Technology", M. S. Patel, F. S. S. Morton and H. Seager, *Manufacturing Chemists*, July 1989; "Soft Elastic Gelatin Capsules: A Unique Dosage Form", William R. Ebert, *Pharmaceutical Technology*, October 1977; "Soft gelatin capsules: a solution to many tableting problems", H. Seager, *Pharmaceutical Technology*, September 1985; U.S. Pat. No. 4,067,960 to Fadda; U.S. Pat. No. 4,198,391 to Grainger; U.S. Pat. No. 4,744,988 to Brox; and U.S. Pat. No. 4,780,316 to Brox. These references are incorporated herein in their entireties by reference.

After the rotary die process is used to thereby produce gelatin shells having a shampoo composition of the instant invention as fill therein, the resulting capsules are typically washed with an evaporatable solvent. Thereafter, the capsules are typically tumble dried in a series of hollow drums with perforated walls. Room air (25° C.) is continuously pumped through the rotating drums. By the time the capsules exit this process, all of the solvent used in washing has typically been evaporated, and a large proportion (50–60%) of the water from the gelatin shell has been removed. Recent developments in drying include bypassing the drum drying stage and having the capsules dried in a drying tunnel or room as discussed below.

After the capsules exit the last drying drum, the capsules are typically spread on drying trays. The final drying phase for softgels is typically accomplished by passing the drying trays through drying tunnels or into drying rooms. Stacks of trays are inserted into drying tunnels or drying rooms, in which controlled temperature air (21°–24° C.) and low relative humidity (20–30%) is continuously circulated. Although additional water may be removed from dry capsules by further heating, for example at 40° C., such a procedure has not been found to be practical or necessary. See Van Hostetler and J. Q. Bellard in *The Theory and Practice of Industrial Pharmacy*, "Capsules", (1970), Chapter 13 at pages 346–383, and in particular at page 380.

The drying time, for most softgels, is 16–24 hours, but may be slightly longer if the softgels are over 20 minims in size or if the softgels contain a non-oily type liquid base. The Karl Fischer test is used for determining water content. The drying occurs typically at about 21°–24° C. and at a relative humidity of 20–40%.

Softgels permitted to come to water equilibrium in this controlled environment are considered "dry". After drying, the capsules are typically inspected and finished using varied known techniques.

A typical gelatin shell formulation includes 47 wt % gelatin, 15 wt % glycerin (USP), and 38 wt % water, optionally with additional colorant materials. Other shell formulations can readily be prepared by one of ordinary skill in the art.

Softgels having the inventive shampoo compositions as fill are capable of being stored for extended periods of time, typically up to 24–36 months or longer, at room temperature (25° C.).

The invention is further illustrated by reference to the following non-limiting examples.

EXAMPLE 1 Shampoo conditioner formulation

| Ingredient | Amount (wt %) |
| --- | --- |
| Polyethylene glycol 400 | 52.45 |
| Polyquaternium 10 | 3.00 |
| PEG-7 glyceryl cocoate | 5.00 |
| Cocamide DEA | 5.00 |
| Ethoxylated methyl glucoside | 2.00 |
| Tocopherol | 0.50 |
| Bisabolol | 0.05 |
| Sodium laureth sulfate (70% concentration) | 30.00 |
| Perfume oil | 2.00 |

EXAMPLE 2 Shampoo conditioner formulation

| Ingredient | Amount (wt %) |
| --- | --- |
| Polyethylene glycol 400 | 51.95 |
| Polyquaternium 10 | 3.00 |
| PEG-7 glyceryl cocoate | 5.00 |
| Cocamide DEA | 5.00 |
| Ethoxylated methyl glucoside | 2.00 |
| Tocopherol | 0.50 |
| Bisabolol | 0.05 |
| Sodium laureth sulfate (70% concentration) | 30.00 |
| Citric acid (50% solution) | 0.50 |
| Perfume oil | 2.00 |

EXAMPLE 3 Shampoo conditioner formulation

| Ingredient | Amount (wt %) |
| --- | --- |
| Polyethylene glycol 400 | 52.50 |
| Polyquaternium 10 | 3.00 |
| PEG-7 glyceryl cocoate | 5.00 |
| Cocamide DEA | 5.00 |
| Ethoxylated methyl glucoside | 2.00 |
| Tocopherol | 0.50 |
| Sodium laureth sulfate (70% concentration) | 30.00 |
| Perfume oil | 2.00 |

EXAMPLE 4 Shampoo conditioner formulation

| Ingredient | Amount (wt %) |
| --- | --- |
| Polyethylene glycol 400 | 49.95 |
| Polyquaternium 10 | 5.00 |
| PEG-7 glyceryl cocoate | 5.00 |
| Cocamide DEA | 5.00 |
| Ethoxylated methyl glucoside | 2.00 |
| Tocopherol | 0.50 |
| Bisabolol | 0.05 |
| Sodium laureth sulfate (70% concentration) | 30.00 |
| Citric acid (50% solution) | 0.50 |
| Perfume oil | 2.00 |

What is claimed is:

1. A hair care product comprising a shampoo conditioner composition encapsulated in a gelatin shell, said shampoo conditioner composition comprising about 10 to about 40 wt % of a concentrated surfactant selected from the group consisting of sodium laureth sulfate, sodium lauryl sulfate, ammonium lauryl sulfate, sodium oleyl succinate, triethanolamine oleate and combinations thereof, about 1 to 5 wt % of a quaternary ammonium salt cationic conditioner, and about 35–60 wt % of a polyethylene glycol carrier having a weight average molecular weight from about 200 to about 800, said composition having a viscosity from about 5000 to 8000 cps, an equilibrium relative humidity between about 65% and 35%, and less than 3 wt % free water.

2. The hair care product of claim 1 wherein said concentrated surfactant is concentrated sodium laureth sulfate.

3. The hair care product of claim 1 wherein said cationic conditioner is polyquaternium-10.

4. The hair care product of claim 1 wherein said composition further comprises a humectant.

5. The hair care product of claim 4 wherein said humectant is selected from the group consisting of PEG-7 glyceryl cocoate, cocomide DEA, an ethoxylated methyl glucoside and combinations thereof.

6. The hair care product of claim 1 wherein said composition further comprises an additive selected from the group consisting of a non-cationic conditioner, a pH adjuster, a foam enhancer, a clarifier and a fragrance.

7. The hair care product of claim 6 wherein said non-cationic conditioner is selected from the group consisting of Vitamin E and bisabolol.

8. The hair care product of claim 4 wherein said composition comprises about 1 to about 15 wt % of a humectant or combination of humectants.

9. The hair care product of claim 1 wherein said composition comprises (a) polyquaternium-10 in an amount from about 1 to about 5 wt %;

(b) a humectant selected from the group consisting of PEG-7 glyceryl cocoate, cocomide DEA, ethoxylated methyl glucoside and combinations thereof in an amount from about 1 to about 15 wt %;

(c) sodium laureth sulfate in an amount from about 10 to about 40 wt %;

(d) citric acid in an amount from 0 to about 0.5 wt %;

(e) an additive selected from the group consisting of Vitamin E and bisabolol and combinations thereof in an amount from 0 to about 2 wt %;

(f) fragrance in an amount from 0 to about 2 wt %; and (g) the balance of PEG-8.

10. The hair care product of claim 1 which is stable for at least 24 months at a temperature of about 25° C.

11. A method of shampooing hair comprising the steps of dispensing the composition encapsulated in the hair care product of claim 1 from said gelatin shell, applying said composition to said hair which has been wet with water, working said composition through said hair, and rinsing said composition from said hair.

12. A hair care product comprising a shampoo conditioner composition encapsulated in a gelatin shell, said shampoo conditioner composition comprising about 10 to about 40 wt % of a concentrated surfactant selected from the group consisting of sodium, magnesium, ammonium and mono-, di- and triethanolamine salts of sulfated fatty alcohols, sodium, magnesium, ammonium and mono-, di- and triethanolamine salts of sulfonated alkaryl compounds and combinations thereof, said compounds having a total of from 12 to 21 carbon atoms and combinations thereof, about 1 to 5 wt % of a cationic conditioner selected from the group consisting of quaternary ammonium salts, amine salts, quaternary imidazoline compounds and combinations thereof, and about 35–60 wt % of a polyalkylene glycol carrier having a weight average molecular weight from about 200 to about 800, said composition having a viscosity from about 5000 to 8000 cps, an equilibrium relative humidity between about 65% and 35%, and less than 3 wt % free water.

13. The hair care product of claim 12 wherein said composition further comprises a humectant.

14. The hair care product of claim 13 wherein said humectant is selected from the group consisting of PEG-7 glyceryl cocoate, cocomide DEA, an ethoxylated methyl glucoside and combinations thereof.

15. The hair care product of claim 12 wherein said composition further comprises an additive selected from the group consisting of a non-cationic conditioner, a pH adjuster, a foam enhancer, a clarifier and a fragrance.

16. The hair care product of claim 15 wherein said non-cationic conditioner is selected from the group consisting of Vitamin E and bisabolol.

17. The hair care product of claim 12 wherein said composition comprises about 1 to about 15 wt % of a humectant or combination of humectants.

18. The hair care product of claim 12 which is stable for at least 24 months at a temperature of about 25° C.

19. A method of shampooing hair comprising the steps of dispensing the composition encapsulated in the hair care product of claim 12 from said gelatin shell, applying said composition to said hair which has been wet with water, working said composition through said hair, and rinsing said composition from said hair.

* * * * *